US00PP28535P3

(12) United States Plant Patent
Klemm et al.

(10) Patent No.: US PP28,535 P3
(45) Date of Patent: Oct. 17, 2017

(54) ***DAHLIA* PLANT NAMED 'KLEDH15076'**

(50) Latin Name: ***Dahlia* sp.**
Varietal Denomination: KLEDH15076

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 19 days.

(21) Appl. No.: 14/998,562

(22) Filed: Jan. 19, 2016

(65) Prior Publication Data

US 2017/0208725 P1 Jul. 20, 2017

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — Barbara Campbell; James M. Weatherly; Cochran Freund & Young, LLC

(57) ABSTRACT

A new *dahlia* plant particularly distinguished by purple-red flowers with white tips, a compact, semi-upright habit, and free basal branching, is disclosed.

1 Drawing Sheet

Genus and species: *Dahlia* sp.
Variety denomination: 'KLEDH15076'.

BACKGROUND OF THE NEW PLANT

The present invention comprises a new and distinct variety of *Dahlia*, botanically known as *Dahlia* sp., and hereinafter referred to by the variety name 'KLEDH15076'. 'KLEDH15076' originated from a cross-pollination conducted in September 2011 in Stuttgart, Germany between the proprietary female *dahlia* variety 'DH-2010-0173 (FA)' (unpatented) and the proprietary male *dahlia* variety 'DH-20000-Bicolor red (5)' (unpatented).

The seeds from the cross-pollination were sown and plants were grown in a greenhouse for evaluation, where an individual plant designated 'KLEDH15076' was selected from the group in May 2012 of plants in Stuttgart, Germany. In May 2012, 'KLEDH15076' was first vegetatively propagated by terminal cuttings. 'KLEDH15076' was found to reproduce true to type in successive generations of asexual propagation via terminal cuttings.

SUMMARY

The following are the most outstanding and distinguishing characteristics of this new variety when grown under normal horticultural practices in Stuttgart, Germany.

1. Purple-red flowers with white tips;
2. A compact, semi-upright habit; and
3. Free basal branching.

CROSS-REFERENCE TO RELATED APPLICATIONS

An application for plant breeders rights for the instant variety has been filed with the Canadian Plant Breeders Rights Office on Apr. 2, 2015, Application No. 15-8576.

DESCRIPTION OF THE PHOTOGRAPH

The following detailed descriptions set forth the distinctive characteristics of 'KLEDH15076'. The data which define these characteristics were collected from asexual reproductions carried out in Stuttgart, Germany. Data was collected on three-month-old plants grown indoors in Stuttgart, Germany under greenhouse conditions in April 2015.

Color references are to The R.H.S. Colour Chart of The Royal Horticultural Society of London (R.H.S.), 5$^{th}$ edition (2007).

DESCRIPTION OF THE NEW VARIETY

The following detailed descriptions set forth the distinctive characteristics of 'KLEDH15076'. The data which define these characteristics were collected from asexual reproductions carried out in Kenya in winter 2014 to 2015. Data was collected on 2.5-month old plants grown in a controlled greenhouse environment approximating those generally used in commercial production, pinched once, with a growth regulator, and under natural light. Color references are to The R.H.S. Colour Chart of The Royal Horticultural Society of London (R.H.S.), 5$^{th}$ edition (2007).

Classification:
- *Family.*—Asteraceae.
- *Botanical.*—*Dahlia* sp.
- *Common.*—*Dahlia.*
- *Designation.*—'KLEDH15076'.

Parentage:
- *Female parent.*—The proprietary female *dahlia* variety 'DH-2010-0173 (FA)' (unpatented).
- *Male parent.*—And the proprietary male *dahlia* variety 'DH-20000-Bicolor red (5)' (unpatented).

Plant:
- *Plant and growth habit.*—Compact, semi-upright, free basal branching, and inflorescences held above the foliar plane.
- *Height.*—About 22.0 cm.
- *Diameter.*—About 30.0 cm.
- *Propagation.*—Terminal cuttings.
- *Time to produce a rooted young plant.*—3 to 4 weeks.

*Root description.*—Medium thickness and light tan in color, RHS 158.

*Rooting habit.*—Freely branching and moderately dense.

Lateral branches:

*Length.*—6.0 cm to 10.0 cm.

*Diameter.*—About 0.3 cm.

*Internode length.*—2.0 cm to 4.0 cm.

*Aspect.*—Outwardly spreading.

*Strength.*—Strong.

*Texture.*—Smooth.

*Color.*—RHS 144B.

Foliage/leaves:

*Arrangement.*—Leaves are opposite, pinnately compound.

*Length.*—About 12.0 cm.

*Width.*—About 12.0 cm.

*Shape.*—Oval.

*Apex.*—Acute.

*Base.*—Acute.

*Margin.*—Moderately serrate.

*Immature leaf color.*—Upper surface: RHS 139B. Lower surface: RHS 139C.

*Mature leaf color.*—Upper surface: RHS 139B. Lower surface: RHS 139C.

*Texture* (*both upper and lower surfaces*).—Pilose.

*Venation pattern.*—Pinnate.

*Venation color* (*both surfaces*).—RHS 143B.

*Petioles.*—Length: 3.0 cm to 4.0 cm. Diameter: 0.3 cm. Texture (both upper and lower surfaces): Smooth. Color: Upper surface: RHS 143C. Lower surface: RHS 141D.

Buds:

*Height.*—About 1.0 cm.

*Diameter.*—About 1.5 cm.

*Shape.*—Oblate.

*Color.*—RHS 143C.

Inflorescence:

*Appearance and arrangement.*—Daisy-eyed double inflorescences held above the foliar plane.

*Fragrance.*—Absent.

*Time to flower.*—In the winter, about 3 months after planting; in the summer, about 2 months after planting.

*Post-production longevity.*—Plants flower continuously from spring through autumn.

*Inflorescence diameter.*—About 10.0 cm.

*Inflorescence depth.*—About 6.0 cm.

*Disc diameter.*—About 2.0 cm.

*Receptacle height.*—About 1.0 cm.

*Receptacle diameter.*—4.0 cm to 5.0 cm.

*Receptacle color.*—RHS 144A and RHS 144B.

Ray florets:

*Quantity per inflorescence.*—About 50 arranged in about 3 to 4 whorls.

*Length.*—About 4.0 cm.

*Width.*—About 2.5 cm.

*Shape.*—Elliptic.

*Apex.*—Obtuse.

*Base.*—Rounded.

*Margin.*—Entire.

*Aspect.*—Semi-upright.

*Texture* (*both upper and lower surfaces*).—Smooth.

*Color, both mature and immature.*—Upper surface: RHS 60B, tips are RHS 69C. Lower surface: RHS 60C, tips are RHS 69C.

Disc florets:

*Quantity per inflorescence.*—About 60.

*Length.*—About 1.0 cm.

*Diameter.*—0.2 cm.

*Shape.*—Tubular.

*Texture* (*both the upper and lower surfaces*).—Smooth.

*Color, immature* (*both upper and lower surfaces*).—RHS 12B.

*Color, mature* (*both upper and lower surfaces*).—RHS 12C.

Phyllaries:

*Quantity per inflorescence.*—5 to 6.

*Length.*—About 1.5 cm.

*Width.*—About 0.8 cm.

*Shape.*—Elliptic.

*Apex.*—Acute.

*Base.*—Acute.

*Margin.*—Entire.

*Texture* (*both upper and lower surfaces*).—Smooth.

*Color.*—Upper surface: RHS 141B. Lower surface: RHS 141C.

Peduncles:

*Length, terminal peduncle.*—Up to 12.0 cm.

*Length, axillary peduncle.*—5.0 cm to 12.0 cm.

*Diameter.*—0.3 cm.

*Aspect.*—Semi-upright.

*Strength.*—Strong.

*Texture.*—Smooth.

*Color.*—RHS 143B with some anthocyanin, RHS 183C.

Reproductive organs:

*Androecium.*—Present on disc florets only. Quantity per floret: 4. Filament length: 0.3 cm. Filament color: RHS 4D. Anther shape: Long lanceolate. Anther length: 0.5 cm. Anther color: RHS 14C. Pollen amount: Abundant. Pollen color: RHS 21A.

*Gynoecium.*—Quantity per floret: 1. Pistil length: 1.2 cm. Style length: 0.5 cm. Style color: RHS 8D. Stigma shape: Lanceolate pinnate. Stigma color: RHS 16D. Ovary color: RHS 8D.

Fruit and seed set: No fruit and seed set observed.

Disease and pest/insect resistance: No disease and pest/insect resistance observed except for moderate resistance to powdery mildew (no special species were observed).

COMPARISON WITH PARENTAL LINE AND KNOWN VARIETY

'KLEDH15076' is a distinct variety of *dahlia* and is distinguished from its parents as described in Table 1.

TABLE 1

| Comparison with Parental Lines | | | |
|---|---|---|---|
| Characteristic | 'KLEDH15076' | Female Parent 'DH-2010-0173 (FA)' | Male Parent 'DH-2000-Bicolor red (5)' |
| Ray floret color | Purple-red with white tips | Purple | Red with white tips |

'KLEDH15076' is a distinct variety of *dahlia* and is most similar to the commercial *dahlia* variety 'Starlias Bi-Color Red White' (unpatented). Differences between the varieties are described in Table 2.

TABLE 2

| Comparison with Similar Variety | | |
|---|---|---|
| Characteristic | 'KLEDH15076' | 'Starlias Bicolor Red-White' |
| Mildew resistance | Moderate resistance | Susceptible |

We claim:

1. A new and distinct variety of *dahlia* plant designated 'KLEDH15076' as illustrated and described herein.

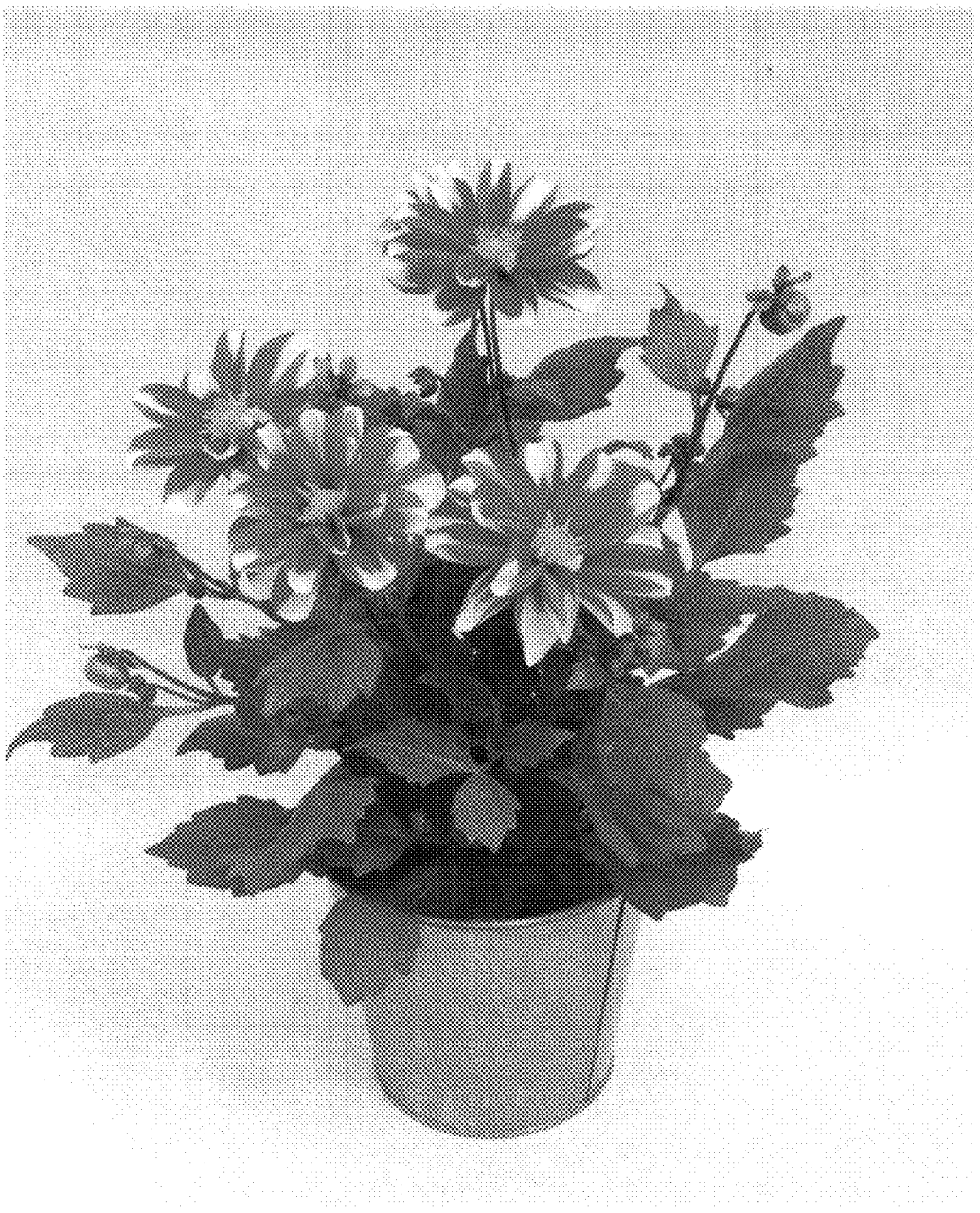

* * * * *